United States Patent [19]

Kaplan et al.

[11] Patent Number: 4,501,745

[45] Date of Patent: Feb. 26, 1985

[54] ANXIOLYTIC IMIDAZO[1,2-A]PYRIDINE DERIVATIVES

[75] Inventors: Jean-Pierre Kaplan, Bourg-la-Reine; Pascal George, Vitry sur Seine, both of France

[73] Assignee: Synthelabo, Paris, France

[21] Appl. No.: 484,591

[22] Filed: Apr. 13, 1983

[30] Foreign Application Priority Data

Apr. 21, 1982 [FR] France .................. 82 06840

[51] Int. Cl.³ .................. A61K 31/435; C07D 409/04
[52] U.S. Cl. .................. 514/222; 514/231; 514/234; 514/300; 544/58.4; 544/127; 544/362; 546/121
[58] Field of Search .............. 546/121; 544/58.4, 127, 544/362; 424/256, 246, 248.52, 248.5, 248.51, 248.53, 248.54, 250

[56] References Cited

U.S. PATENT DOCUMENTS 4,382,938  5/1983  Kaplan et al. .................. 546/121

FOREIGN PATENT DOCUMENTS 1076089  7/1967  United Kingdom .

OTHER PUBLICATIONS

Almirante et al., J. Med. Chem., vol. 12, 1969, pp. 123–126.

*Primary Examiner*—Henry R. Jiles
*Assistant Examiner*—Bernard I. Dentz
*Attorney, Agent, or Firm*—Wegner & Bretschneider

[57] ABSTRACT

Imidazo[1,2-a]pyridine derivatives of the general formula:

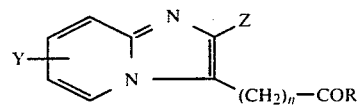

wherein n represents 2, 3 or 4, Y represents a hydrogen or halogen atom or a $C_{1-4}$ alkyl radical, Z represents a naphthyl radical; a phenyl radical

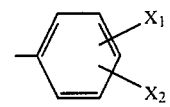

in which $X_1$ and $X_2$ independently of one another each represent a hydrogen or halogen atom, a $C_{1-4}$ alkoxy radical, a $C_{1-6}$ alkyl radical or the group $-CF_3$, $CH_3S-$, $CH_3SO_2-$ or $-NO_2$; or a thien-2-yl, furan-2-yl or pyridin-2-yl radical optionally carrying a halogen atom or the methyl or ethyl radical in the 5-position, and R represents the hydroxy radical, or a group $-NR_1R_2$ in which $R_1$ and $R_2$ independently of one another each represent a hydrogen atom; a straight- or branched-chain $C_{1-5}$ alkyl radical optionally carrying one or more halogen atoms, a hydroxy radical, a group $-N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical; or alternatively $-NR_1R_2$ together represent a heterocyclic ring containing from 3 to 6 carbon atoms, or a heterocyclic ring of the formula

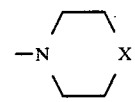

in which X is O, S, CHOR' or NR", R' being a hydrogen atom or the benzyl radical and R" being a hydrogen atom, a $C_{1-4}$ alkyl radical or the phenyl radical optionally carrying a methoxy radical or a halogen atom, are new compounds. They are therapeutically useful as they possess anxiolytic, antianoxic, sleep-inducing, hypnotic and anticonvulsant properties.

9 Claims, No Drawings

ANXIOLYTIC IMIDAZO[1,2-A]PYRIDINE DERIVATIVES

DESCRIPTION

The present invention relates to new therapeutically useful imidazo[1,2-a]pyridine derivatives, to processes for their preparation and to pharmaceutical compositions containing them.

Imidazo[1,2-a]pyridines have already been described in the literature, for example in British Patents 991589 and 1076089 and in various other publications.

The imidazo[1,2-a]pyridine derivatives of the present invention are those compounds of the general formula:

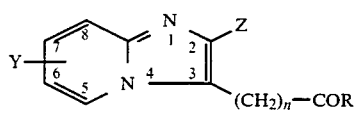

(I)

wherein n represents 2, 3 or 4, Y represents a hydrogen or halogen (preferably chlorine) atom or a $C_{1-4}$ alkyl (preferably methyl) radical, Z represents a naphthyl radical; a phenyl radical

in which $X_1$ and $X_2$ independently of one another each represent a hydrogen or halogen (preferably chlorine) atom, a $C_{1-4}$ alkoxy radical, a $C_{1-6}$ alkyl (preferably methyl) radical or the group —$CF_3$, $CH_3S$—, $CH_3SO_2$— or —$NO_2$; or a thien-2-yl, furan-2-yl or pyridin-2-yl radical optionally carrying a halogen atom or the methyl or ethyl radical in the 5-position, and R represents the hydroxy radical, or a group —$NR_1R_2$ in which $R_1$ and $R_2$ independently of one another each represent a hydrogen atom; a straight- or branched-chain $C_{1-5}$ alkyl radical optionally carrying one or more halogen atoms, a hydroxy radical, a group —$N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical; or alternatively —$NR_1R_2$ together represent a heterocyclic ring containing from 3 to 6 carbon atoms, or a heterocyclic ring of the formula

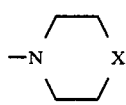

in which X is O, S, CHOR′ or NR″,R′ being a hydrogen atom or the benzyl radical and R″ being a hydrogen atom, a $C_{1-4}$ alkyl radical or the phenyl radical optionally carrying a methoxy radical or a halogen atom, and pharmaceutically-acceptable acid addition salts thereof.

The preferred compounds of the invention are those of general formula (I) wherein n represents 2 and, more particularly, those wherein Y is in the 6-position and represents either a halogen atom or the methyl radical.

Amongst the latter, there may be mentioned in particular the compounds wherein Z represents either a phenyl radical

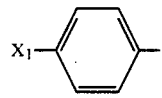

in which $X_1$ represents a halogen (preferably chlorine) atom or the methyl radical, or the grouping

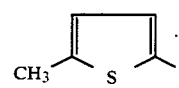

Preferably the symbol, R represents the hydroxy radical, or a group —$NR_1R_2$ in which $R_1$ and $R_2$ both represent hydrogen atoms or both represent $C_{1-5}$ alkyl radicals, for example the dimethylamino group.

Outstanding compounds of the present invention are 6-methyl-N,N-dimethyl-2-(4-methylphenyl)-imidazo[1,2-a]pyridine-3-propionamide and 6-methyl-2-(5-methylthien-2-yl)-imidazo[1,2-a]pyridine-3-propionamide, and their pharmaceutically-acceptable acid addition salts.

According to a feature of the invention, the imidazo[1,2-a]pyridine derivatives of general formula (I) are prepared according to the following general reaction scheme:

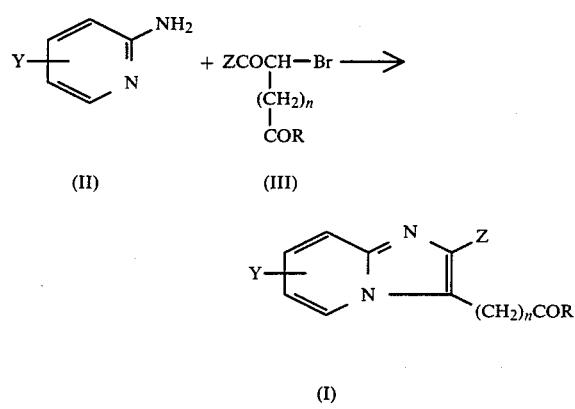

wherein n, Y, Z and R are as hereinbefore defined.

The 2-aminopyridine of general formula (II) is reacted with the bromoketone of general formula (III) in an organic solvent such as ethanol or dioxan.

According to another feature of the invention, the compounds of general formula (I) wherein n represents 2, are also prepared according to the following particular reaction scheme:

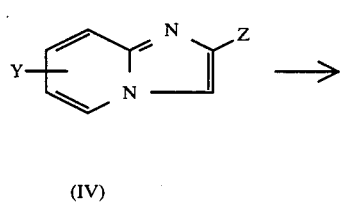

(IV)

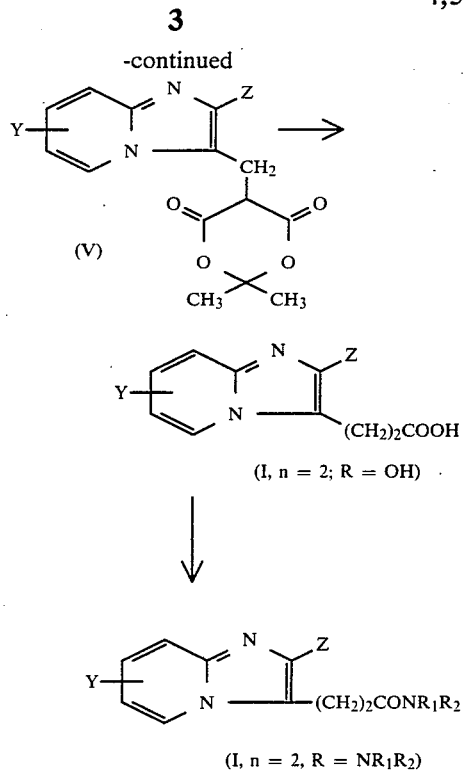

wherein the various symbols are as hereinbefore defined.

The imidazo[1,2-a]pyridine starting compound of general formula (IV) is reacted with 2,2-dimethyl-1,3-dioxacyclohexane-4,6-dione in the presence of a 30% aqueous solution of formaldehyde and in an organic solvent such as acetonitrile; the resulting compound of general formula (V) is then heated in the presence of copper powder, in pyridine and water, to give a compound of general formula (I) wherein R is the hydroxy radical, and, if desired, the acid obtained is converted to an amide by methods known per se.

The starting compounds of general formula (IV) can be prepared by reacting a 2-aminopyridine of general formula (II) with a bromoketone of the general formula $ZCOCH_2Br$, wherein Z is as hereinbefore defined.

Pharmaceutically-acceptable acid addition salts of the imidazo[1,2-a]pyridine derivatives of general formula (I), e.g. methanesulphonates, mandelates, fumarates, maleates, malonates, citrates, hydrochlorides, hydrobromides and hydroiodides may be obtained by methods known per se, for example by treatment of the imidazo[1,2-a]pyridine base with the appropriate acid in a solvent medium, e.g. an alkanol or ether, or mixtures thereof.

By the term 'methods known per se' as used in this specification is meant methods heretofore used or described in the literature.

The Examples which follow illustrate the invention.

The analyses and the IR and NMR spectra confirm the structures of the compounds.

EXAMPLE 1

6-Chloro-2-(4-chlorophenyl)-imidazo[1,2-a]-pyridine-3-propionic acid

[Y=6—Cl, Z=4—Cl—$C_6H_4$, R=OH]

1. 50 g (0.19 mol) of 6-chloro-2-(4-chlorophenyl)-imidazo[1,2-a]pyridine, 21 g (0.021 mol) of a 30% aqueous solution of formaldehyde and 27.4 g (0.19 mol) of 2,2-dimethyl-1,3-dioxacyclohexane-2,4-dione are heated in 1 liter of acetonitrile for 4 hours at 60° C., with stirring. After cooling, the cold reaction mixture is filtered and the product is washed with acetone and then with methylene chloride and diethyl ether. The product conforming to formula (V) is dried at 45°–50° C. in vacuo for 8 hours.

Melting point=134°–135° C.

2. 45 g (0.107 mol) of the compound obtained in step 1, 300 cc of pyridine and 30 cc of water are heated, in the presence of 0.5 g of copper powder, for 3 hours at the reflux temperature, under nitrogen. The reaction medium is filtered hot and the filtrate is evaporated to dryness. The residue is triturated in 500 cc of a 5% solution of ammonium chloride.

The crystalline solid is filtered off and washed with water. The crude acid obtained is suspended in 1 liter of water, and 15 g of sodium carbonate and 5 ml of concentrated aqueous ammonia solution are added to the suspension. The mixture is heated at the reflux temperature for 30 minutes, with stirring. The resulting suspension of the sodium salt of the acid is filtered cold.

The salt is then introduced into 1 liter of water at 50°–60° C., and the solution is acidified to pH 5.5-6 by adding acetic acid, with stirring.

After stirring for 1 hour at ambient temperature, the acid is filtered off, washed 3 times with water and then with acetone and dried for 8 hours at 100° C. in vacuo.

Melting point of the title product=278°–280° C.

EXAMPLE 2

6-Methyl-2-(4-methylphenyl)-imidazo[1,2-a]-pyridine-3-propionamide

[Y=6—$CH_3$, Z=4—$CH_3$—$C_6H_4$, R=$NH_2$]

1. 30 g (0.135 mol) of 6-methyl-2-(4-methylphenyl)-imidazo[1,2-a]pyridine, 19.45 g (0.135 mol) of 2,2-dimethyl-1,3-dioxacyclohexane-2,4-dione, 15 g (0.15 mol) of a 30% aqueous solution of formaldehyde and 500 cc of acetonitrile are heated for 4 hours at 55°–60° C.

After cooling, the reaction mixture is filtered cold and the product obtained is washed with acetone and then with diethyl ether and dried.

Melting point of product=182°–184° C.

2. 45 g (0.119 mol) of the compound otained in step 1 are heated with 0.5 g of copper powder, in 300 cc of pyridine and 30 cc of water, for 3 hours at the reflux temperature, under nitrogen. The reaction mixture is filtered hot and 200 cc of a 5% solution of ammonium chloride are added.

The reaction mixture is concentrated to about 100 cc by evaporation. After the addition of 500 cc of water, the resulting suspension is heated at 60°–70° C. for 1 hour, with stirring.

After cooling, the mixture is filtered cold and the product is washed with a 5% solution of $NH_4Cl$ and then 3 times with water.

After washing with acetone and then with diethyl ether, the product is dried for 8 hours at 80° C. in vacuo.

Melting point of the acid product=255°–257° C.

3. 6.5 g (0.04 mol) of carbonyldiimidazole are added to a suspension of 10 g (0.034 mol) of the acid obtained in step 2 in 200 cc of dry tetrahydrofuran (THF). After stirring for 2 hours at 50° C. under dry nitrogen, a gentle stream of excess ammonia gas is passed in. The reaction mixture is left to stand overnight and then evaporated to dryness. The residue is washed with 200 cc of a boiling 5% solution of potassium carbonate. The mixture is filtered hot and this hot washing is repeated twice more and the residue is then washed 3 times with water and dried. The product is recrystallised from a 90/10 ethanol/methylcellosolve mixture, washed with diethyl ether and dried at 100° C. in vacuo for 8 hours.

Melting point of the title product=232°-233° C. (decomposition).

The imidazo[1,2-a]pyridine derivatives identified in the following Table were prepared, by way of examples, according to the same reaction scheme.

TABLE

| Compound | n | Y | Z | R | Melting point (°C.) |
|---|---|---|---|---|---|
| 1 | 2 | 6-Cl | 4-Cl—$C_6H_4$ | OH | 278-280 |
| 2 | 2 | 6-Cl | 4-Cl—$C_6H_4$ | $NH_2$ | 259-260 |
| 3 | 2 | 6-Cl | 4-Cl—$C_6H_4$ | $N(CH_3)_2$ | 150.5-151 |
| 4 | 2 | 6-$CH_3$ | 4-$CH_3$—$C_6H_4$ | OH | 255-257 |
| 5 | 2 | 6-$CH_3$ | 4-$CH_3$—$C_6H_4$ | $NH_2$ | 232-233 |
| 6 | 2 | 6-$CH_3$ | 4-$CH_3$—$C_6H_4$ | $N(CH_3)_2$ | 171-172 |
| 7 | 2 | 6-$CH_3$ | $CH_3$—thienyl | OH | 226-228 |
| 8 | 2 | 6-$CH_3$ | $CH_3$—thienyl | $NH_2$ | Base: 220-221  HCl: 258-260 |
| 9 | 2 | 6-$CH_3$ | $CH_3$—thienyl | $N(CH_3)_2$ | 141.5-142 |

The compounds of the invention were subjected to pharmacological tests, which showed their valuable pharmacological properties in various fields.

The toxicity of the compounds was determined on mice by intraperitoneal administration. The LD50 ranges from 500 to 1000 mg/kg animal body weight.

The anxiolytic activity was determined by the "eating test" (R. J. Stephens (1973) Brit. J. Pharmac., 49, 146 P). In this test, the doses which increase the food consumption of the mice vary from 1 to 30 mg/kg, administered intraperitoneally.

The activity of the compounds in the field of the brain circulation was determined in the test for hypoxia caused by pressure reduction.

Mice of the CD1 strain are kept in an oxygen-depleted atmosphere produced by creating a partial vacuum (190 mm of mercury, corresponding to 5.25% of oxygen).

The survival time of the animals is noted. This time is increased by agents which are capable of assisting the oxygenation of tissues and in particular of the brain. The compounds studied are administered intraperitoneally in several doses, 10 minutes before the test. The percentage increases in the survival time, relative to the values obtained for control animals, are calculated. The mean active dose (MAD), that is to say the dose which increases the survival time by 100%, is determined graphically. The MAD ranges from 0.3 to 32 mg/kg, administered intraperitoneally.

The anticonvulsant activity was determined by the test for antagonism towards the mortality induced by bicuculline in mice (P. Worms, H. Depoortere and K. G. Lloyd (1979) Life Sci., 25, 607–614). The products to be studied are injected intraperitoneally, 30 minutes before the bicuculline (0.9 mg/kg, administered intravenously). As the criterion chosen for this test is lethality, the percentage mortalities are noted for each batch, 2 hours after administration of the bicuculline (control batch: 100% mortality).

The 50% active dose (AD50, that is to say the dose which protects 50% of animals from the lethal effects of the bicuculline) is determined graphically for each product. The AD50 of the compounds of the invention varies between 1 and 30 mg/kg, administered intraperitoneally.

The sedative or hypnotic activity was determined by observing the action of the compounds on the ECG of curarised rats (H. Depoortere, Rev. E.E.G. Neurophysiol., (1980) 10, 3, 207–214). The products to be studied were injected intraperitoneally or orally into the curarised rats, at increasing doses from 1 to 30 mg/kg. They induce sleep traces as from doses ranging from 1 to 10 mg/kg, administered intraperitoneally or orally.

The results of these various tests show that the compounds of the invention possess anxiolytic, antianoxic, sleep-inducing, hypnotic and anticonvulsant properties. The compounds of the invention are useful for the treatment of anxiety states, sleep disorders and other neurological and psychiatric complaints, for the treatment of vigilance disorders, in particular for combating the behavioural disorders attributable to cerebral vascular damage and to the cerebral sclerosis encountered in geriatrics, and also for the treatment of the absences due to cranial traumatisms and for the treatment of metabolic encephalopathies.

The present invention consequently includes within its scope pharmaceutical compositions containing, as active ingredient, an imidazo[1,2-a]pyridine derivative of general formula (I), or a pharmaceutically acceptable acid addition salt thereof, in association with any suitable excipient.

The compounds of the invention can be presented in any form suitable for oral or parenteral administration, for example in the form of tablets, coated tablets, gelatine capsules, solutions to be taken orally or injected, and the like, with any suitable excipient.

The daily dosage can range from 0.5 to 2000 mg of imidazo[1,2-a]pyridine derivative.

We claim:

1. An imidazo[1,2-a]pyridine derivative of the formula:

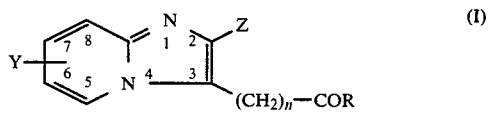

wherein n represents 2, 3 or 4, Y represents a hydrogen or halogen atom or a $C_{1-4}$ alkyl radical, Z represents a thien-2-yl, furan-2-yl or pyridin-2-yl radical optionally carrying a halogen atom or the methyl or ethyl radical in the 5-position, and R represents the hydroxy radical, or a group —$NR_1R_2$, in which $R_1$ and $R_2$ independently of one another each represent a hydrogen atom; a straight- or branched-chain $C_{1-5}$ alkyl radical optionally carrying one or more halogen atoms, a hydroxy radical, a group —$N(C_{1-4}$ alkyl$)_2$, a carbamoyl radical or a $C_{1-4}$ alkoxy radical; the allyl radical; the propargyl radical; a $C_{3-6}$ cycloalkyl radical; the benzyl radical; or the phenyl radical; or alternatively —$NR_1R_2$ together represent a heterocyclic ring containing from 3 to 6 carbon atoms, or a heterocyclic ring of the formula

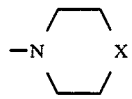

in which X is O, S, CHOR' or NR", R' being a hydrogen atom or the benzyl radical and R" being a hydrogen atom, a $C_{1-4}$ alkyl radical or the phenyl radical optionally carrying a methoxy radical or a halogen atom, and pharmaceutically-acceptable acid addition salts thereof.

2. An imidazo[1,2-a]pyridine derivative according to claim 1 wherein n represents 2.

3. An imidazo[1,2-a]pyridine derivative according to claim 2 wherein Y is in the 6-position of the depicted ring structure and represents either a halogen atom or the methyl radical.

4. An imidazo[1,2-a]pyridine derivative according to claim 1 wherein Z represents the grouping

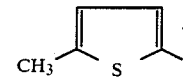

5. An imidazo[1,2-a]pyridine derivative according to claim 1 wherein R represents the hydroxy radical, or a group —$NR_1R_2$ in which $R_1$ and $R_2$ both represent hydrogen atoms or both represent $C_{1-5}$ alkyl radicals.

6. An imidazo[1,2-a]pyridine derivative according to claim 5 wherein R represents a dimethylamino group.

7. An imidazo[1,2-a]pyridine derivative according to claim 4 which is 6-methyl-2-(5-methylthien-2-yl)-imidazo[1,2-a]pyridine-3-propionamide and its pharmaceutically-acceptable acid additional salts.

8. An anxiolytic pharmaceutical composition comprising an anxiolytically effective amount of imidazo[1,2-a]pyridine derivative as claimed in claim 1, or a pharmaceutically-acceptable acid addition salt thereof, in association with a pharmaceutically-acceptable vehicle.

9. A method for the treatment of anxiety states, sleep disorders and other neurological and psychiatric complaints, for the treatment of vigilance disorders, in particular for combating the behavioural disorders which can be attributed to cerebral vascular damage and to the cerebral sclerosis encountered in geriatrics, and also for the treatment of the absences due to cranial traumatisms and for the treatment of metabolic encephalopathies, which comprises administering to a patient with such an ailment an amount of an imidazo[1,2-a]pyridine derivative of the formula depicted in claim 1 or a pharmaceutically-acceptable acid addition salt thereof, sufficient to ameliorate the condition of the patient.

* * * * *